(12) United States Patent
Meilland et al.

(10) Patent No.: US 7,489,129 B2
(45) Date of Patent: Feb. 10, 2009

(54) METHOD AND SYSTEM FOR THE DETECTION OF SURFACE DEFECTS ON A METAL PRODUCT AS IT IS BEING CONTINUOUSLY CAST

(75) Inventors: Philip Meilland, Entrange (FR); Jean-Michel Turon, Plappeville (FR); Fabien Midroit, Metz (FR)

(73) Assignee: ArcelorMittal France, Saint Denis (FR)

( * ) Notice: Subject to any disclaimer, the term of this patent is extended or adjusted under 35 U.S.C. 154(b) by 0 days.

(21) Appl. No.: 10/579,533

(22) PCT Filed: Oct. 29, 2004

(86) PCT No.: PCT/FR2004/002802

§ 371 (c)(1),
(2), (4) Date: Jan. 24, 2007

(87) PCT Pub. No.: WO2005/052569

PCT Pub. Date: Jun. 9, 2005

(65) Prior Publication Data

US 2007/0285088 A1    Dec. 13, 2007

(30) Foreign Application Priority Data

Nov. 18, 2003    (FR) .................................. 03 13498

(51) Int. Cl.
*G01N 27/72*    (2006.01)

(52) U.S. Cl. ....................... 324/228; 324/238; 324/239; 324/240

(58) Field of Classification Search ......... 324/219–221, 324/232, 238, 225, 239, 240, 242, 243, 241, 324/260–262, 228
See application file for complete search history.

(56) References Cited

U.S. PATENT DOCUMENTS

| | | | |
|---|---|---|---|
| 5,047,719 A | 9/1991 | Johnson et al. | |
| 5,237,271 A | 8/1993 | Hedengren | |
| 5,262,722 A | 11/1993 | Hedengren et al. | |
| 5,390,109 A * | 2/1995 | Takemoto et al. | 324/207.11 |
| 5,506,503 A | 4/1996 | Cecco et al. | |
| 6,172,499 B1 * | 1/2001 | Ashe | 324/207.12 |
| 6,339,327 B1 | 1/2002 | Potiquet et al. | |
| 6,344,739 B1 * | 2/2002 | Hardy et al. | 324/220 |

* cited by examiner

*Primary Examiner*—Reena Aurora
(74) *Attorney, Agent, or Firm*—Sughrue Mion, PLLC

(57) ABSTRACT

The invention relates to a method of detecting surface defects on a continuously-cast crude metallic product, such as a steel slab (4). According to the invention, a sensor (10) is used to detect surface defects by means of eddy currents, said sensor consisting of a matrix comprising at least two rows (22, 24) of at least three adjoining measuring cells (21) which can be controlled by a multiplexing control unit (12). Moreover, each cell can generate eddy currents at the surface of the slab and, alternately, detect eddy currents in said surface. The inventive method comprises a step consisting in controlling a first transmitting cell and a second receiving cell from the same row, but which are separated from one another by at least one inactive cell.

7 Claims, 2 Drawing Sheets

METHOD AND SYSTEM FOR THE DETECTION OF SURFACE DEFECTS ON A METAL PRODUCT AS IT IS BEING CONTINUOUSLY CAST

The invention relates to the detection of surface defects on a slab, or, more generally, on a metal product, especially a steel product, as it is being continuously cast.

More precisely, the invention relates to the detection of surface defects on a metal product as it is being continuously cast using an eddy current sensor with a separate transmitter and receiver, these being placed facing each other and close to the surface to be inspected.

FR 84/14435 discloses a sensor of this type, also called an "EC (eddy current) sensor with anisotropic probes", the probes of which are separate transmitting and receiving coils, a certain distance from each other along a line oriented perpendicular to the travel of the slab that is passing beneath them. Such a sensor is therefore sensitive to the modifications in the flow of the eddy currents that are generated by the presence of a long defect transverse to the surface of the product inspected. It thus makes it possible in particular to discriminate transverse edge cracks since the induced currents generated beneath the transmitter by the magnetic field of the latter do not flow right beneath the receiver defects when propagating from one to the other are absent.

However, since the distance separating the two coils, namely the transmitter coil and the receiver coil, is fixed by construction, just short cracks are therefore detected if a sufficiently extended region of the slab edge is not scanned, either by multiple passes of the sensor with an accordingly adjusted lateral incremental shift, or by placing a series of multiple sensors side by side so that the whole assembly covers the region in question.

The invention aims to solve these difficulties by making use of recent high-speed imaging technologies using arrays (or rows) of elementary mini-coils (or cells) that are aligned and can be separately activated by programmed multiplexing. Examples of eddy current sensors of this type may be found for example in the following documents: FR 93/00984, U.S. Pat. Nos. 6,339,327 and 5,237,271, these being used for the inspection of metal sheet, plate or strip in many technical fields.

Depending on its mode of activation, each cell is thus capable of either generating or detecting eddy currents on the surface of the metal product to be inspected. Consequently, by activating first and second contiguous cells of the row, one so as to generate eddy currents and the other for detecting them, it is possible to determine the presence or otherwise beneath the sensor of elongate surface defects that would propagate from one to another. The pair of activated cells is stepwise offset by one cell along the row at each iteration of this control step, so as to scan and inspect the entire surface of the metal plate facing this row of cells without either moving the plate to be inspected or the sensor. To obtain good spatial resolution and to be able to detect defects of the order of a few millimeters, the size of the cells, the general shape of which is square, is of the order of a few square millimeters.

The metal plates inspected with such sensors must be smooth and the measurement cells are placed at a distance of less than 1.5 millimeters from the surface of the plate to be inspected. At such a distance from the surface of the plate, the sensors rapidly and accurately detect any surface defect manifested by a break in electrical conductivity. However, beyond this distance these sensors become inaccurate and unusable. Attempts at using these same sensors for detecting cracks on the surface of steel slabs obtained directly by continuous casting have hitherto, to the knowledge of the Applicant, met with failure. This is because the surface asperities of the slab together with the high temperature of this slab, which is generally above 550° C., mean that it is barely possible to keep the sensor for a long time at less than 1.5 mm from the surface to be inspected.

The invention aims to remedy such a handicap so as to be able to use these EC sensors with rows of cells activated by multiplexing on a metal product in its continuously cast state.

Thus, one subject of the invention is a method for detecting surface defects on a metal product as it is being continuously cast, using an eddy current sensor of the "separate transmitter/receiver" type having rows of contiguous aligned measurement cells that are separately controllable by multiplexing, the product to be inspected undergoing a traveling movement relative to the sensor, characterized in that, said sensor comprising a matrix of measurement cells distributed in rows and columns, and said matrix having at least first and second parallel rows of at least three measurement cells each, the multiplexing is activated in successive control steps in such a way that:

in a given control step, first and second cells in each row are activated, these cells being separated from each other by at least one inactive measurement cell, the first cell being activated so as to generate eddy currents on the surface of said metal product and the second being activated so that it detects the eddy currents generated by the first cell, the flow of which currents on the surface has been modified by the presence of surface defects, and, at predetermined time intervals, the two activated cells are inactivated and said control step is repeated with two following cells, which are offset by at least one cell along the same row relative to the two inactivated cells, and so on, until the surface region to be inspected has been checked; and in that said control step is carried out simultaneously for the first and second rows of cells, said first cells of each row belonging to just one column and said second cells of each row also belonging to just another column, said second cells of each row being configured so as to produce signals of opposite polarity when a defect is detected.

In other words, the cell that generates the eddy currents must always be faced away from the cell that detects them in the same row by at least one inactive cell. This is because it has been discovered that increasing the spacing between the two activated cells, namely the transmitting cell and the receiving cell, makes it possible to increase the distance separating these cells from the surface to be inspected, while maintaining the performance of the sensor at a sufficient level for the intended application. It is therefore possible to use cells at a distance of more than 1.5 millimeters from the surface of the slab, thereby making it possible to use these sensors to detect surface cracks on metal products obtained directly from the continuous casting of a slab.

Moreover, the control step is carried out simultaneously and in exactly the same manner on the two adjacent rows, the pairs of active cells in the second row being however configured so as to produce signals of reverse polarity with respect to the pair of active cells for the first row. This makes it possible, by adding the signals, to obviate the inevitable perturbations arising for example from oscillation marks present on the surface of the cast slab and to deliver, to the inspector, a very clean defect detection signal with minimal background noise.

The subject of the invention is also a defect detection system comprising a sensor for detecting surface defects by eddy currents, of the "separate transmitter/receiver" type, comprising at least two rows of at least three measurement cells each contiguous and controllable, and a programmable multiplexing control unit suitable for controlling said measurement cells, each cell being capable of generating or detecting eddy currents, characterized in that the two rows of cells are placed side by side parallel to each other and in that said control unit is a multiplexer control unit capable of activating a first and second cell of a row that are separated from each other by at least one inactive measurement cell and of activating, in the same manner, but with the reverse polarity, the corresponding analogous cells in the second row.

According to other preferred features of the system according to the invention, this is characterized in that:

the sensor is provided with a plane base in which said rows of cells flush with the surface are housed, said base being intended to be placed at a distance of at least three millimeters from the surface to be inspected;

the sensor includes a circuit for cooling the base with a circulating coolant; and the cooling circuit includes at least one ceramic plate placed facing the base so as to leave a space for circulation of the coolant.

The invention will be better understood and other aspects and advantages will become more clearly apparent on reading the description given by way of example and with reference to the appended plates of drawings in which.

Figure 1:
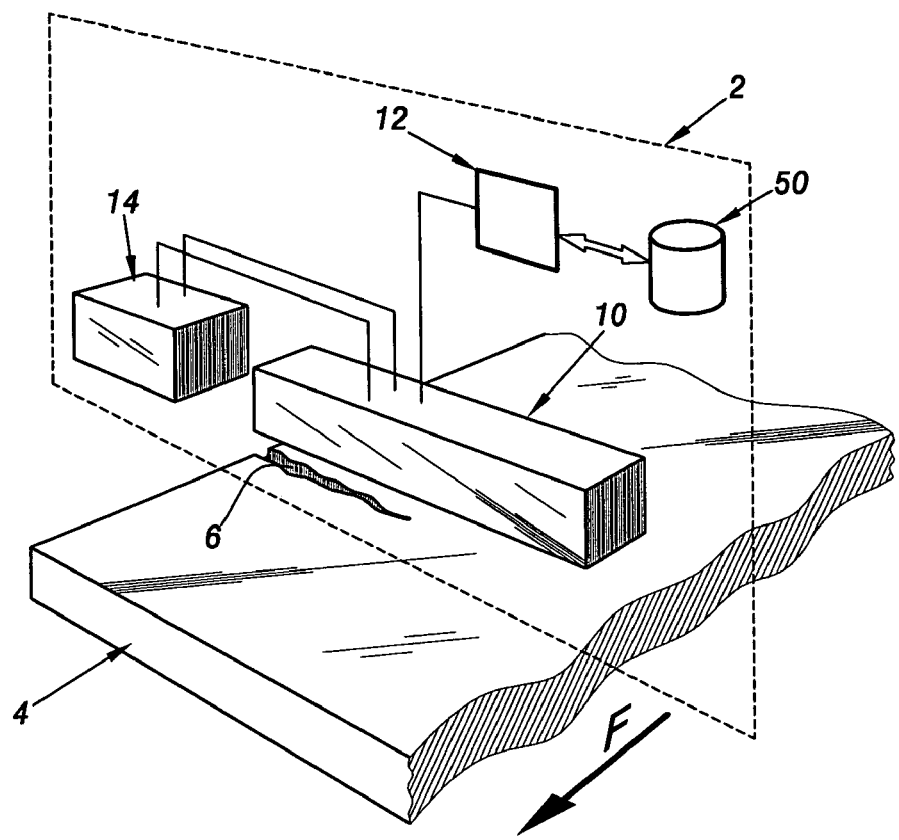
FIG. 1 is a schematic illustration of a detection system according to the invention.

FIG. 1 shows a system 2 for the continuous detection of surface defects of a steel slab 4 obtained directly from a continuous casting installation. The slab 4 lies in a horizontal plane and it is in this configuration that it achieves a slow forward movement (barely a little more than 1 m/min), beneath the sensor 2. To simplify the illustration of FIG. 1, only the upper left edge of the slab 4 has been shown.

The slab 4 is what is called here a product as it is being continuously cast.

At the point where the detection system 2 is placed, the slab typically still has a temperature of above 550° C. Its upper surface facing the sensor 2 is irregular, having numerous asperities and local reliefs such as mold oscillation marks or scale islands, and also, as the case may be, long surface defects to be detected, such as various transverse cracks, crevices or notches. These surface defects result in a local break in the conductivity of the surface of the slab 4. It should be noted that this break in conductivity does not necessarily mean the presence of a flaw on the surface of the slab 4. Here, only a transverse crack 6 has been shown. This crack 6 is called a transverse crack as it extends in a direction perpendicular to the travel direction of the slab 4. The travel direction of the slab 4 is shown by the arrow F in FIG. 1.

To make it easier to install the detection system 2 in an environment where the temperature rises to above 550° C., the system has no moving parts and only the slab 4 moves translationally beneath it in the travel direction F.

The system 2 comprises a sensor 10, a control unit 12 for controlling the sensor, and a coolant delivery pump 14. The sensor 10 is capable of detecting conductivity defects on the surface of the slab 4 by means of eddy currents. As the operating principle of such a sensor is known, it will not be explained in detail here. The reader may for example refer to European patent application EP 0 195 794 for more information about the operating principles of such sensors.

Here, the sensor 10 has the form of a rectangular parallelepiped oriented perpendicular to the travel direction F, one face (called the "active face", since the measurement cells are flush with its surface) of which is placed parallel to the surface of the slab 4. This sensor 10 is placed so that its active face is "astride" the edge of the slab 4 so as always to be able to inspect the outermost edge, even were the traveling product to undergo slight lateral deviation in its travel.

Figure 2:
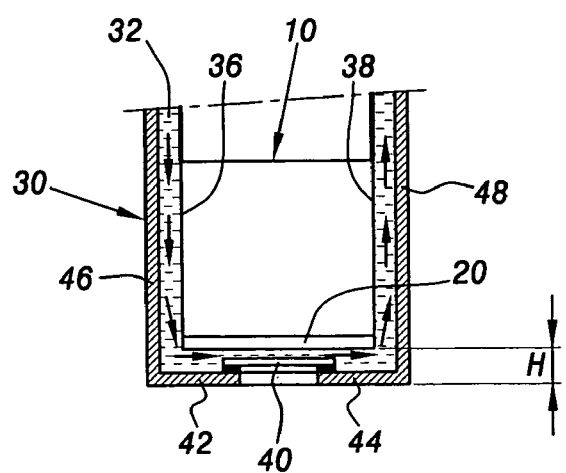
FIG. 2 is a vertical sectional view of the cross section of an eddy current sensor for detecting surface defects using the system of FIG. 1.

As illustrated in FIG. 2, the active face of the sensor 20 is formed by a base 20 in which measurement cells 21 are housed.

Figure 3:
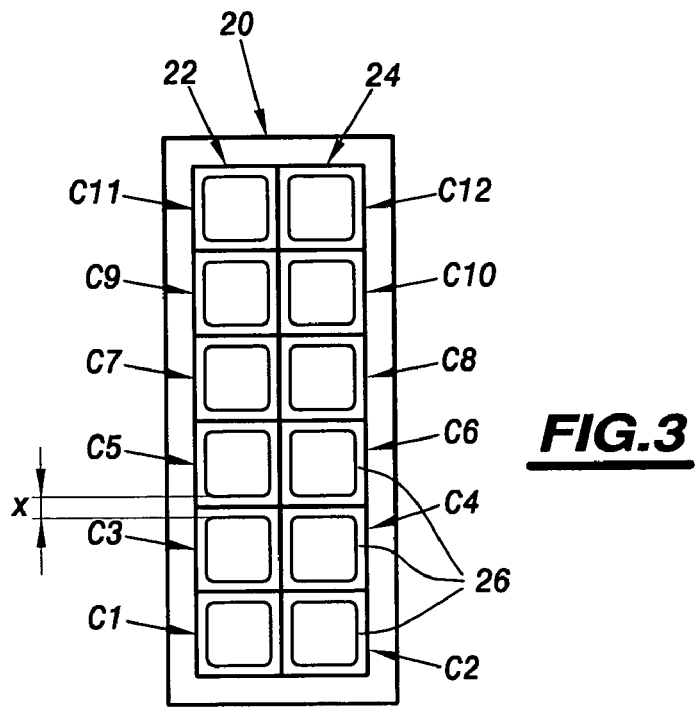
FIG. 3 is a schematic illustration of the active part of the sensor of FIG. 2.

The lower surface of this base 20 is shown in FIG. 3. This base 20 has, by way of illustration, two identical rows 22 and 24 of measurement cells 21, all being identical to one another. These two rows are located parallel to each other in the length direction of the sensor 10. These rows 22 and 24 are also arranged as close as possible to each other so that their respective cells are placed alongside one another and touch one another, at least on one side.

To simplify the illustration, only six measurement cells 21 have been shown in each row. In reality, a row may comprise up to thirty-two, or more, cells. Here, the cells of the row 22 are denoted, in order, starting from the bottom and going upward, by the references C1, C3, C5, C7, C9 and C11 respectively. Similarly, the cells of the row 24 are denoted, in order and starting from the bottom upward, by the references C2, C4, C6, C8, C10 and C12 respectively.

Each of the measurement cells 21 is suitable for being configured, under the control of the unit 12, either as a transmitting cell or as a receiving cell.

When the cell 21 is configured as a transmitting cell, this is capable of creating eddy currents in the surface of the slab 4. For this purpose each cell comprises a coil 26 supplied with AC current. The axis of this coil 26 is perpendicular to the active face of the sensor 10.

When the cell is configured as a receiving cell, this is capable of detecting eddy currents present in the surface of the slab 4, if, and only if, the eddy currents created by the transmitting cell have been deflected toward the receiving cell by a surface defect that propagates from one cell to the other, according to the principle explained in the abovementioned EP 0 195 794. For this purpose, the coil 26 forms a closed electrical circuit used for detecting electromagnetic fields.

As already indicated, the contiguous cells of the rows 22 and 24 are also capable of being connected up in differential mode one with respect to another on the two rows so as to eliminate measurement or detection errors due to surface irregularities on the slab 4, such as oscillation marks. More precisely, the cells of each row 22 and 24 configured as receiving cells are capable of generating signals for detecting a surface defect, of opposite polarity. This has the consequence that, when a receiving cell of the row 22 detects a fault, it generates a signal, for example of positive polarity, whereas the corresponding receiving cell of the row 24 generates a detection signal of negative polarity when it detects the same defect.

Here, typically, the cells 21 are to be detaching and the coils 26 of the contiguous cells are separated from one another by an edge-to-edge gap X of less than 0.5 mm and preferably about 0.2 mm. This closeness of the various coils 26 makes it possible to ensure almost continuous scanning and inspection of the surface of the slab over the entire length of the rows 22 and 24.

In order to maximize the overall sensitive area of the sensor, the cells 21 are square in shape, like their internal coil 26. In addition, to detect surface defects or cracks whose length barely exceeds 4 millimeters, each of these coils has a square cross section of 4×4 mm².

To protect the base 20 from the heat, the sensor 10 is also equipped with a device 30 (FIG. 2) for cooling the base 20. This device 30 includes a circuit 32 for circulating a coolant. This circuit 32 descends along a vertical wall 36 of the sensor 10, passes beneath the base 20 and comes back up along another vertical wall 38 of the sensor 10. To provide the part of the circuit 32 which passes beneath the base 20, the device 30 includes a rectangular plate 40 placed facing and parallel to the base 20 so as to protect the measurement cells. This plate is, for example, made of a ceramic so as to be permeable to the electromagnetic waves generated and received by the coils 26 of the various measurement cells. This plate 40 is, for example, placed at about 1 millimeter from the surface of the base 20. It is kept in position by two horizontal feet 42 and 44 fastened along its long sides. The feet 42 and 44 are intended to slide over the surface of the slab 4 and act as runners. These horizontal feet 42 and 44 are each integral with a vertical metal plate 46 and 48 respectively.

The plates 46 and 48 lie along the walls 36 and 38 of the sensor 10. They are spaced away from the vertical walls 36 and 38 so as to leave a space for passage of the circuit 32. To withstand the heat, the feet 42 and 44 and the plates 46 and 48 are, for example, made of stainless steel. The thickness of the feet 42 and 44, the thickness of the plate 40 and the thickness of the circuit 32 beneath the base 20 are chosen in such a way that the height H separating the base 20 from the upper surface of the slab 4 is equal to or greater than three millimeters and preferably greater than 4 millimeters.

The arrows shown in the circuit 32 indicate the direction of circulation of the coolant. Here, the coolant is water. Each end of the circuit 32 is connected to the pump 14, suitable for circulating the coolant in the circuit 32.

The control unit 12 is a multiplexer capable of individually controlling each of the cells of the base 20. This control unit consists, for example, of a conventional programmable electronic computer combined with a memory 50, having instructions for executing the method shown in FIG. 4.

Figure 4:
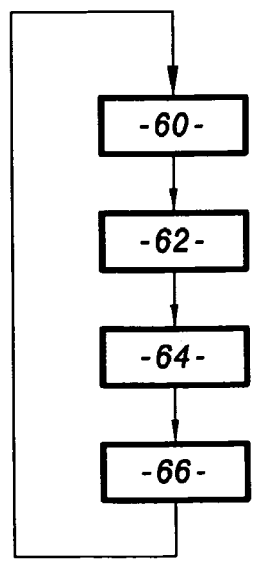
FIG. 4 is a flow diagram of a surface defect detection method according to the invention.

The operation of the system will now be described with regard to the method shown in FIG. 4. During operation of the system 2, the slab 4 travels, flat, beneath the sensor 10 in the direction of the arrow F. Here, when an edge crack 6 occurs beneath the base 20, one of the cells of the row 24 detects this crack and generates a corresponding signal. The crack 6 is then detected by at least one of the cells of the other row 22, which also generates a corresponding signal, but of opposite polarity.

The operation of the sensor 10 activated by the multiplexer 12 is divided into a number of timeslots, each timeslot corresponding to a predefined time interval. In each timeslot, only one pair of cells of the row 22 and one pair of cells of the row 24 are activated, whereas all the other cells of the rows 22 and 24 are inactive. In the inactive state, the coil 26 of the cells is an open coil. This prevents problems of crosstalk between the coils 26 of the various cells.

More precisely, in order for the sensor 10 to be able to operate reliably at more than three millimeters above the surface of the slab 4, the control unit 12 operates as follows. In a first timeslot, the unit 12 configures, during a step 60, the cells C1 and C2 as transmitting cells in order for them to generate eddy currents in the upper surface of the slab 4. At the same time, the unit 12 configures the cells C5 and C6 for them to detect eddy currents in the surface of the slab 4. By controlling the sensor 10 in this way, the transmitting and receiving cells are separated from each other by an inactive cell, in this case the cells C3 and C4. During the first timeslot, the edge-to-edge spacing between the transmitting and receiving cells is therefore greater than four millimeters.

It has been found experimentally that the height at which the base 20 may be placed relative to the surface of the slab 4 increases proportionally with the edge-to-edge spacing between the transmitting cells and the receiving cells. Thus, by providing, during step 60, a space between the transmitting and receiving cells of at least four millimeters, the operation of the sensor 10 is not degraded although it is placed about three millimeters from the surface in which it is sought to detect defects.

Next, during a following, second timeslot, the unit 12 configures, during a step 62, the cells C3 and C4 and the cells C7 and C8 so that the cells C3 and C4 work at the same time as transmitting cells, whereas the cells C7 and C8 work at the same time as receiving cells. At the same time, the other cells, and in particular the previously activated cells, that is to say the cells C1, C2, C5 and C6, are made inactive.

During the next, third, timeslot, step 62 is repeated during a step 64, while shifting the actuated cells by one cell upward. Consequently, during this step 64, it is the cells C5 and C6 that work as transmitting cells and the cells C9 and C10 that work as receiving cells.

During the next timeslot, the unit 12 proceeds to step 66, identical to the previous steps except that it is the cells C7, C8, C11 and C12 that are activated. The procedure then returns to step 60.

Steps 60, 62, 64 and 66 are repeated as long as the system 2 is operating. It is thus found that, by shifting by one cell the cells activated during each of the steps 60, 62, 64 and 66, it is possible to scan the entire surface portion of the slab facing the base 20 with a high resolution, since the cross section of the cells is of the order of 4 mm², and without thereby moving the sensor 10.

Thus, such a control method makes it possible to detect, with high resolution, defects on a surface as wide as the sensor is long, and to do so during a single pass beneath the sensor. Another advantage of the system 2 is that it is insensitive to the position of the edge of the slab 4 relative to the position of the base 20. In other words, the measurement cells of the base 20 that are outside the surface of the slab, that is to say beyond the upper edge of the slab 4, do not impede the operation of the sensor 10 at all, so that it is unnecessary for the slab 4 to be precisely positioned with respect to this sensor 10.

The operation of the system 2 has been described in the particular case in which, during each timeslot, the transmitting and receiving cells are separated only by a single inactive cell. So as to increase the spacing between the transmitting and receiving cells, and therefore to offer the possibility of placing the sensor 10 at an even greater distance H from the surface of the slab, as a variant, the transmitting and receiving cells in any one row may be separated from one another by one, two, three, four or five inactive cells.

Moreover, it is possible to increase the detection capabilities of the device by providing a larger number of rows of cells than two.

It is also unnecessary for the rows of cells to be contiguous. A gap may be provided between them.

The system 2 has been described in the particular case in which it is placed in an environment in which the temperature may be above 550° C. The same system may of course be used for inspecting a slab at room temperature. In this variant, the device 30 for cooling the base is unnecessary and can therefore be omitted.

The system 2 has been described in the particular case in which the coils have a cross section of 16 mm². As a variant, and depending on the length of the defects to be detected, each coil may have an oblong, or more precisely a rectangular, cross section, the short and long sides of this rectangle having a length of between 2 and 10 mm.

The invention claimed is:

1. A method for detecting surface defects on a metal product as it is being continuously cast, using an eddy current sensor of the separate transmitter/receiver type having rows of contiguous aligned measurement cells that are separately controllable by multiplexing, the product to be inspected undergoing a traveling movement relative to the sensor, wherein, said sensor comprising a matrix of measurement cells distributed in rows and columns, and said matrix having at least first and second parallel rows of at least three measurement cells each, the multiplexing is activated in successive control steps in such a way that:

in a given control step, first and second cells in each row are activated, these cells being separated from each other by at least one inactive measurement cell, the first cell being activated so as to generate eddy currents on the surface of said metal product and the second being activated so that it detects the eddy currents generated by the first cell, the flow of the eddy currents on the surface being modified by the presence of surface defects, and, at predetermined time intervals, the two activated cells are inactivated and said control step is repeated with two following cells, which are offset by at least one cell along the same row relative to the two inactivated cells, and so on, until the surface region to be inspected has been checked; and wherein said control step is carried out simultaneously for the first and second rows of cells, said first cells of each row belonging to just one column and said second cells of each row also belonging to just another column, said second cells of each row being configured so as to produce signals of opposite polarity when a defect is detected.

2. A system for detecting surface defects on a metal product as it is being continuously cast, comprising a sensor for detecting surface defects by eddy currents, of the separate transmitter/receiver type comprising a matrix of measurement cells distributed in rows and columns, said matrix having at least first and second parallel rows of at least three measurement cells each that are contiguous and controllable, and a unit for controlling the sensor, by multiplexing, suitable for controlling said measurement cells, each measurement cell being capable of generating eddy currents on the surface of said metal product to be inspected and, alternately, of detecting eddy currents on said surface, said system being wherein the control unit with multiplexer is capable of controlling:

first and second cells in each row, which are separated from each other by at least one inactive measurement cell, the first cell being activated so as to generate eddy currents on the surface of said metal product and the second being activated so as to detect the eddy currents generated by the first cell, the flow of the eddy currents on the surface being modified by the presence of surface defects; and the at least three measurement cells of the second of said first and second parallel rows in the same way as the at least three measurement cells of the first of said first and second parallel rows.

3. The system as claimed in claim 2, wherein the sensor includes a base in which at least three aligned rows are housed and in that the base is placed at a distance of at least three millimeters from the surface on which the surface defects have to be detected.

4. The system as claimed in claim 3, further including a device for cooling the base.

5. The system as claimed in claim 4, wherein the cooling device includes a circuit for circulating a coolant along the base.

6. The system as claimed in claim 5, wherein the cooling device includes at least one ceramic plate placed facing the base so as to leave a space for the coolant circulation circuit.

7. The system as claimed in claim 2, wherein each cell of the first row is contiguous with a cell of the second row and can be configured so as to deliver a signal of opposite polarity to that delivered by the contiguous cell of the second row, and in that the control unit is suitable for configuring the second cells of the first and second rows so that they deliver signals of opposite polarity.

* * * * *